Figure 1:
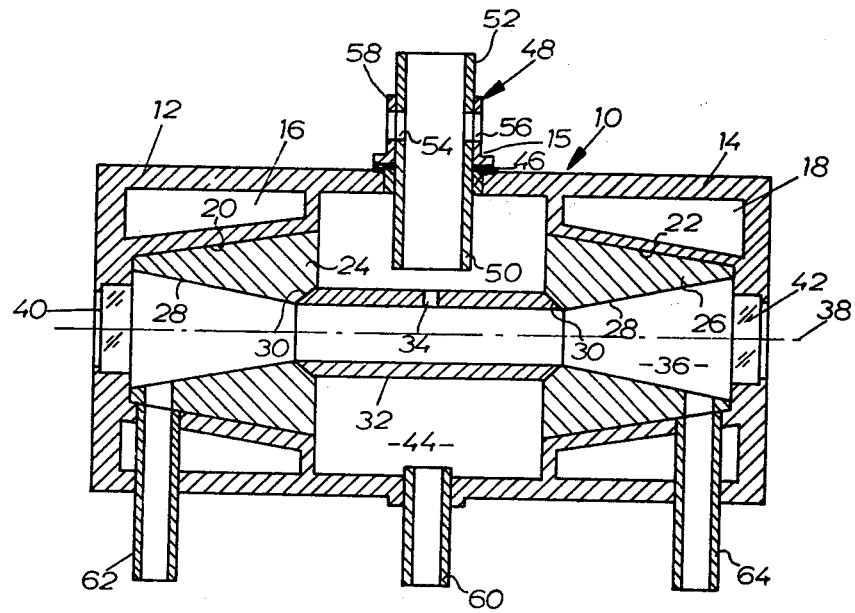

United States Patent [19]

Huber et al.

[11] 4,098,554
[45] Jul. 4, 1978

[54] DEVICE FOR ATOMIZING A SAMPLE FOR FLAMELESS ATOMIC ABSORPTION MEASUREMENTS

[75] Inventors: Bernhard Werner Huber, Uberlingen; Rolf Günter Tamm, Salem; Klaus Joachim Braun, Uberlingen, all of Germany

[73] Assignee: The Perkin-Elmer Corporation, Norwalk, Conn.

[21] Appl. No.: 453,114

[22] Filed: Mar. 20, 1974

[30] Foreign Application Priority Data

Mar. 22, 1973 [DE] Fed. Rep. of Germany ....... 2314207

[51] Int. Cl.² .......................... G01J 3/02; G01J 3/30
[52] U.S. Cl. ....................................... 356/85; 356/244
[58] Field of Search ......................... 356/85, 244, 246

[56] References Cited

U.S. PATENT DOCUMENTS

| | | | |
|---|---|---|---|
| 3,702,219 | 11/1972 | Braun et al. | 356/85 X |
| 3,778,156 | 12/1973 | Schmedes et al. | 356/85 X |
| 3,979,162 | 9/1976 | George | 356/85 |

FOREIGN PATENT DOCUMENTS

1,117,776  6/1968  United Kingdom.

OTHER PUBLICATIONS

Massman, Spectrochimica Acta, vol. 23B, No. 4, Apr. 1968, pp. 215–226.

Morrison et al., Analytical Chemistry, vol. 42, No. 7, Jun. 1970, pp. 809–811.

*Primary Examiner*—F. L. Evans
*Attorney, Agent, or Firm*—Sal A. Giarrantana; Francis L. Masselle; Edwin T. Grimes

[57] ABSTRACT

A device for atomizing a sample for so-called flameless atomic absorption spectroscopic measurements of the type in which an electrically conducting hollow tube, into which the sample is introduced as by a central port in the side of the tube, is heated by the passage of current from electrodes contacting the ends of the tube. A protective inert gas is caused to surround the interior and exterior of the tube to exclude air to avoid oxidation of the sample tube which may be graphite. The improvement comprises introducing the protective gas into both ends of the sample tube so that it leaves the interior through the central port from which it may be sucked outside of a surrounding housing. The exterior walls of the sample tube may be provided with protective gas either by means of an auxiliary gas flow or by leading the gas from the bore around the outside of the tube before withdrawing it through the surrounding housing. By introducing the gas flow generally from the cooler ends to the hotter medial portion of the tube, decomposition products or samples are not condensed on cooler parts, from which they could later be vaporized and contaminate the atomized sample elements during subsequent analyses.

11 Claims, 2 Drawing Figures

U.S. Patent  July 4, 1978  4,098,554

DEVICE FOR ATOMIZING A SAMPLE FOR FLAMELESS ATOMIC ABSORPTION MEASUREMENTS

This invention relates to an atomizing device for atomizing a sample for flameless atomic absorption spectroscopic measurements, comprising a tube of electrically conducting material for accommodation of a sample, which is heatable by passing an electric current therethrough and has at least one crossbore or port centrally in its generally cylindrical surface. Flow-generating means provide a protective (inert) gas flow within and around the tube as well as through the port.

Atomizing devices of the type indicated are prior art and known as "graphite tube cells" since the tube typically consists of graphite. In conventional graphite tube cells the graphite tube is held by its conical end faces between complementary conical contact surfaces of two annular electrodes. The electrodes are surrounded by annular respective coolant channels through which a cooling fluid may flow, and the whole arrangement is mounted in a housing which is usually of generally cylindrical shape. Via the electrodes a current of high current density is directed through the graphite tube, so that the graphite tube is heated to high temperatures. As is known, the graphite tube has a port centrally in its tubular surface. Through this port a sample can be introduced into the graphite tube, which sample upon heating of the graphite tube is first dried, then ashed, and finally atomized so that the elements contained in the sample are finally rendered in an atomic state. A measuring beam of light of an atomic absorption spectrometer is at this time passed axially through the electrodes and the interior of the graphite tube. In conventional atomic absorption spectrometers the measuring beam of light originates from a line-emitting light source, for instance, a hollow cathode lamp, and contains the resonance line of an element of interest in the sample. The absorption experienced by the measuring beam of light in the atomic cloud then is representative of the quantity of the tested-for element of interest in the sample. To prevent burn-out of the graphite tube during heating, the tube is surrounded on both its interior and exterior by an inert protective gas stream which prevents admission of atmospheric oxygen. This protective gas stream has been commonly directed into an annular chamber which is formed around the graphite tube between the same and the housing. From this annular chamber protective gas passes through the central port into the interior of the graphite tube so that a protective gas stream also flows into the interior of the graphite tube through the central port and then axially towards both ends of the tube (inside thereof) so that admission of atmospheric oxygen is prevented.

Moreover, this protective gas stream has the function during drying or ashing of the sample to "rinse" out of the graphite tube prior to atomization products of evaporation or products of thermal decomposition, which would disturb the absorption measurement of the desired element of interest. After the measurement, a "rinse-out" of the atomic cloud from the tube is also required.

Therefore, the protective gas must expediently have a finite speed of flow at least during specific periods of time of the analytical process. During "rinsing out" of products of evaporation and of decomposition, and of the atomic cloud of the preceding measurement (i.e., preceding sample) difficulties in subsequent measurements can be caused in that the entrained products may deposit at cooler places of the atomizing device. When such places are subsequently heated up again to higher temperatures of the tube, for instance by radiation, such deposited products could be re-vaporized and pass into the optical path of the measuring beam and thus degrade the accuracy of the analytical results. In the described prior arrangement the gaseous and smoke-like products can deposit at the cooler tube ends or on the force-cooled electrodes.

It is therefore an object of this invention in an atomizing device of the type mentioned hereinbefore to so direct the protective gas flow that deposition, if any, of the products entrained by the protective gas flow is only effected at such locations where the re-vaporization of the products does not adversely influence (i.e., affect the absorption of) the measuring beam of light.

This object is achieved in accordance with the invention by flow-generating means which produce a protective gas flow from the ends of the tube axially inwardly through its interior and then outwardly through the central port to the exterior of the tube.

Thus, the protective gas flows within the tube (and thereby in the path of the measuring beam of light), always from the cooler towards the hotter surface areas since, as previously pointed out the temperature of the tube is the highest at the midpoint of its length. Consequently, a deposition of the carried-away products on the inner surface of the electrodes or of the tube cannot take place. If such deposition does take place after passage of the flow through the central port on the cooler housing surfaces for example, these surfaces are outside the path of rays of the measuring beam, so that products possibly re-vaporized will not be able to pass into the path of rays (especially since the gas flow inhibits entry of such vapors back into the interior of the tube).

Preferably, the tube is surrounded by an annular chamber filled with protective gas, into which the central port opens and which is connected to a protective gas outlet. In this manner, the tube is also enveloped by a stream of protective gas on its exterior. The annular chamber may possibly be filled solely by the protective gas which is supplied through the interior of the tube and exiting through the central port.

However, an additional protective gas flow may also be introduced into the annular chamber via a further protective gas inlet. Thereby, a better discharge of the products of evaporation and decomposition entrained by the protective gas is ensured. Moreover, this additional protective gas flow through the annular chamber can be maintained even if, during the actual measurement, the protective gas flow through the interior of the tube (from its ends) is interrupted temporarily, as may be done in order to keep the atomic cloud formed as long as possible in the path of rays. In this way, during such interruptions, the admission of oxygen into the annular chamber is positively prevented and deposits possibly re-vaporized are prevented from diffusing into the tube through the central port.

The protective gas inlet into the annular chamber may be positioned diametrically opposite the protective gas outlet. Advantageously, the central part is then aligned with the protective gas outlet (which leads to the outside of the housing). The protective gas outlet may include a socket projecting into the annular chamber close to the central port. Thereby, the protective gas flow leaving the central port, which entrains products of decomposition or evaporation from the interior of the tube, is prevented from passing into the annular chamber whereby deposition of these products on the surface of the annular chamber might occur.

The protective gas outlet can be connected with a suction pump, for instance, a water-jet pump (aspirator). Since commonly the suction generated by such a pump is too great for the intended purposes and is also hard to regulate, additionally adjustable secondary air openings can be provided in a connection line extending from the protective gas outlet to the suction pump. In this manner, the suction acting at the protective gas outlet can be reduced and regulated accurately.

The atomizing device, similar to prior art arrangements, can be formed such that in a housing of basically cylindrical shape consisting of two halves insulated with respect to each other, in which are arranged annular electrodes which are surrounded by respective annular coolant channels and which hold the atomizing tube between them, an annular chamber being formed between the tube and housing walls. The housing may have light-transmitting windows in coaxial registration with the ends of the tube. Advantageously, in one preferred embodiment a protective gas channel is formed to pass through each of the coolant channels and the electrodes in the vicinity of the housing ends near the (inner) side of the window and opens into the space surrounded by the electrodes.

With a structure including windows, there is no problem of conducting the protective gas flow from the ends of the tube inwardly to the central port. However, it is then necessary to make the atomizing device relatively long to ensure that a sufficient distance between the windows and ends of the sample tube is maintained. Otherwise, there would be the danger that if there is a temporary interruption of the protective gas flow during the atomization and measurement stages of the cycle of operation, the atomic cloud formed might deposit on the windows.

Instead an arrangement may be provided such that, instead of windows, the housing has light-passing openings in coaxial registration with the tube ends, so that an unobstructed axial passage is obtained. Each of the light-passing openings are surrounded by one annular channel into which the protective gas is introduced and from which the protective gas flows through an annular gap radially inwardly into the passage channel. In order to prevent the admission of atmospheric oxygen due to turbulence in the flow with such an arrangement, it is advantageous if an annular chamber gradually enlarging inwardly to the passage channel communicates with the annular gap, radially inwardly. Thereby the flow speed of the radially supplied protective gas flow is reduced progressively so that this protective gas flow is divided without turbulance into streams flowing axially inwardly into the tube and axially outwardly through the housing end openings. Advantageously, the protective gas flow supplied to the annular channels is substantially greater than the flow leaving the interior of the tube through the central port. Thereby, it is ensured that an axially outwardly directed flow occurs at all times so as to block the admission of atmospheric oxygen into the openings. An atomizing device of the type indicated can be made with a smaller axial dimension, while having the same sample tube dimensions, than an arrangement with windows. Also the possibility of an interference by the windows is eliminated. However, a slightly higher consumption of protective gas must be tolerated.

The introduction of the sample into the tube can be effected similarly to the prior art arrangements, that is, through the central port. To facilitate this, it is advantageous if the protective gas outlet is mounted on a sliding cylindrical valve mounted rotatably on the housing, which has a sample injection opening aligned with the central port and a superposed housing aperature when in an open position.

Figure 2:
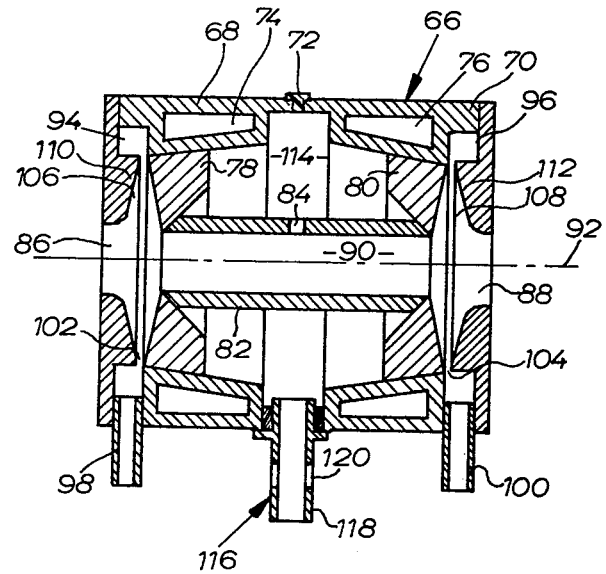

Two illustrative embodiments of this invention will now be described more fully with reference to the accompanying drawings in which:

FIG. 1 is a longitudinal section through an atomizing device provided with windows according to this invention; and FIG. 2 illustrates an alternative atomizing device according to this invention formed without windows.

In FIG. 1, reference numeral 10 designates a housing of generally cylindrical shape consisting of two halves 12, 14. In each of the halves an annular coolant channel 16 and 18, respectively, is provided. The coolant channels 16 and 18 have respective conical inner walls, or contact faces 20, 22. In these contact faces respective graphite electrodes 24, 26 with matching conical outer surfaces are mounted. The graphite electrodes 24 and 26 each have a funnel-shaped inner surface 28 which respectively enlarges towards the respective ends of the housing 10. Moreover, the electrodes 24 and 26 have different funnel-shaped contact faces 30 at the inner edge, which make contact with the matching conical end faces of a graphite tube 32 and hold the graphite tube 32 between them. The graphite tube 32 has a central port 34. In this manner the electrodes 24 and 26 and the graphite tube 32 define a central passage channel 36 for a measuring beam of light represented by axis 38. In the embodiment according to FIG. 1 the passage channel 36 is closed off at both ends by transparent windows 40, 42 mounted in the end faces of the housing halves 12, 14 respectively. An annular chamber 44 is defined between the housing 10 and the graphite tube 32 in a radial direction and between the electrodes 24 and 26 and the coolant channels 16 and 18 in an axial direction.

The two housing halves 12 and 14 are insulated with respect to each other by an insulating bush 46. In the insulating bush 46 a protective gas outlet 48 is provided on one side (top in FIG. 1) in alignment with port 34 of the graphite tube 32. The protective gas outlet includes a socket 50 which extends radially into the annular chamber 44 to closely approach port 34. This socket 50 extends from the housing as a tube connecting socket 52 which may lead to a water-jet (aspirator) pump. The connecting socket 52 contains secondary air openings 54 which are adjustable by a sleeve 58 (mounted on the connecting socket 52) provided with corresponding apertures 56 and rotatable with respect to the socket 52.

A protective gas inlet 60 opens into the annular chamber 44 on the side thereof diametrically opposite to the protective gas outlet 48. Further protective gas connection means 62 and 64 extend through the coolant channels 16, 18 and the electrodes 24, 26 respectively, and open into the passage channel 36 in the vicinity of the two windows 40, 42 respectively.

The desired arrangement operates as follows. A sample is introduced into the graphite tube 32. For this purpose, for instance a hose (not shown) can be pulled off the connecting socket 52 whereupon the sample is injected through the connecting socket 52, the socket 50 and port 34, for instance by means of a syringe. Alternatively, the protective gas outlet with the sockets 52 and 50 may be mounted on a sliding cylindrical slide or valve rotatably supported on the housing, which valve or slide has a sample injection opening aligned with port 34 and a housing aperture thereabove when in an open position. With such a construction the protective gas outlet 48 can simply be moved aside, causing an opening through which the crossbore 34 is made accessible to sample injection.

A protective gas stream flows via the connections 62 and 64 into the passage channel 36 and then axially inwardly through tube 32 to the crossbore 34. It is then sucked off through port 34 via socket 50 and connecting socket 52. Another protective gas stream, introduced into the annular chamber 44 via the connection 60, flows around the graphite tube 32 and then also flows out through the socket 50.

Via the two housing halves 12 and 14 and the electrodes 24, 26 an electric current is supplied to the graphite tube 32 so that the current passing through the length of graphite tube 32 heats it to various elevated temperatures. First, a drying and possibly ashing of the injected sample is effected (at one or two moderately high temperatures); the resulting products of evaporation or decomposition are led off through port 34 by the protective gas flow supplied via the connections 62 and 64 and pass practically directly into the socket 50 of the protective gas outlet. At the same time, protective gas flow is effected via the socket 60, which also flows to the socket 50. Practically no products of evaporation or decomposition pass into the annular chamber 44. Even if this were to occur, these products when re-vaporized could not pass into the path of rays of the measuring beam 38.

Then, a further heating of the graphite tube 32 to a higher temperature is effected by higher electric current, so that the sample in the graphite tube 32 is atomized and the individual elements in the sample prevail in an atomic state for absorption measurement. It is desirable to maintain the atomic cloud thus formed as long as possible in the path of rays of the measuring beam of light 38. For this reason the protective gas supply to the connections 62 and 64 is preferably interrupted during measurement so that therefore during this time no flow occurs in the interior of the graphite tube 32. The flow via connection 60 and annular chamber 44 to the protective gas outlet 48 is still present during this time so that no atmospheric oxygen can pass via the connection 48 into the annular chamber 44 and thus to the glowing graphite tube 32. The electrodes 24, 26 and the housing parts 12, 14 must be relatively long in this closed construction (i.e., with windows 40, 42) in order to ensure that no particles of the atomic cloud diffuse to the windows 40, 42 and possibly deposit there.

Instead of sucking off the protective gas via the socket 48–52 of course, a discharge of the protective gas into the atmosphere can be provided if the protective gas is supplied at the connections 60, 62 and 64 under substantial pressure.

FIG. 2 illustrates an alternative arrangement in which no windows are disposed in the path of the measure beam. It can be seen that with the same overall length graphite tube the length of the apparatus can be reduced substantially.

In FIG. 2 reference numeral 66 designates a housing of basically cylindrical shape which as in the FIG. 1 embodiment consists of two parts or halves 68 and 70 which are electrically insulated with respect to each other by an insulating bush 72. In each of the two housing halves a coolant channel 74 and 76, respectively, is provided. Inwardly of the annular coolant channels, electrodes 78, 80 having conical exterior contact faces are mounted which again hold a graphite tube 82 between them by means of conical interior contact faces. In the graphite tube there is a central port 84.

The housing is provided on its end faces with openings 86, 88 so that an unobstructed passage channel 90 for the measuring beam of light 92 is produced. The openings 86 and 88 are each surrounded by an annular channel 94, 96 respectively into each of which protective gas is introduced via a respective connection 98, 100. This protective gas passes through an annular gap 102, 104, respectively radially inwardly and leaves in the direction towards the passage channel 90 as well as through openings 86 and 88. In order to avoid turbulence, an annular chamber 106, 108, respectively enlarging towards the axis of passage channel 90 follows, in the direction of flow, each of the annular channels 94, 96, and the annular gaps 102, 104, respectively. The chambers 106, 108 are defined by the truncated funnel-shaped outer end face of the electrodes 78, 80, respectively and a correspondingly shaped inner face 110, 112, respectively of the ends of the housing 66. Thereby, a progressive deflection of the protective gas stream leaving through the annular gap 102, 104, respectively, both gradually axially inwardly into the passage channel 90, and gradually axially outwardly through the openings 86 and 88 is effected substantially without turbulence and with a corresponding gradual reduction in the flow speed.

The protective gas entering graphite tube 82 from both ends passes through port 84 into an annular chamber 114 formed between the housing 66, the graphite tube 82 and the electrodes 78 and 80. The protective gas then flows in the annular chamber around the tube 82 and is sucked off through a protective gas outlet 116 diametrically opposite the crossbore 84. The protective gas outlet includes a socket 118 with apertures 120 for aspiration of secondary air in a manner similar to the embodiment according to FIG. 1.

The protective gas volume supplied to the protective gas inlets 98 and 100 is preferably selected at a substantially greater rate than the protective gas volume which is sucked off via the protective gas outlet 116. In this manner it is ensured that an outwardly directed protective gas stream is discharged through the openings 86 and 88 at all times so as to prevent the admission of air.

In the embodiment according to FIG. 2 therefore no separate protective gas stream is introduced into the annular chamber 114. This leads to a saving regarding the consumption of protective gas. On the other hand, more protective gas is required to maintain the flow through the openings 86 and 88. In that no windows according to the windows 40 and 42 of FIG. 1 are required, for the same length of the graphite tube 82, the device can be reduced in its axial dimensions. Since the flow is always from the interior of the tube 82 through port 84 to annular chamber 114 (and then out gas outlet 116) no previous products can inadvertently enter the interior of tube 82 from chamber 114.

The various features of the embodiments according to FIG. 1 and FIG. 2, of course, may also be combined with each other for obtaining specific properties of the atomizing device in various other manners.

What is claimed is:

1. A sample atomizing device for flameless atomic absorption measurements comprising:
a tube of electrically conducting material which is heatable by passing an electric current therethrough, said tube having at least one port exceeding through a wall thereof generally at the longitudinal center of the tube, means for causing the tube to be surrounded by an inert protective gas;
said causing means comprising means for generating a flow of said protective gas generally into the ends of said tube (32, 82) so that the gas flows out of said tube through said central port (34, 84);
housing means (10, 66) generally enclosing said tube to define an annular chamber (44, 114) which surrounds the exterior of said tube and is therefore in communication with said port (34, 84); and
a protective gas outlet means (48, 116) provided so as to allow said protective gas ultimately to flow from said annular chamber (44, 114) to the exterior of said housing;
a second protective gas flow generating means (60) supplying protective gas directly into said annular chamber (44).

2. A sample atomizing device as recited in claim 1, in which:
the inlet into said second protective gas flow generating means (60) is diametrically opposite said protective gas outlet means (48).

3. A sample atomizing device for flameless atomic absorption measurements comprising:
a tube of electrically conducting material which is heatable by passing an electric current therethrough, said tube having at least one port extending through a wall thereof generally at the longitudinal center of the tube, means for causing the tube to be surrounded by an inert protective gas;
said causing means comprising for generating a flow of said protective gas generally into the ends of said tube (32, 82) so that the gas flows out of said tube through said central port (34, 84);
housing means (10, 66) generally enclosing said tube to define an annular chamber (44, 114) which surrounds the exterior of said tube and is therefore in communication with said port (34, 84); and
a protective gas outlet means (48, 116) provided so as to allow said protective gas ultimately to flow from said annular chamber (44, 114) to the exterior of said housing;
said protective gas outlet means (48) being directly aligned with said central port (34) of said tube (32); and
said protective gas outlet means (48) including a portion (50) which projects inwardly into said annular chamber (44) so as to terminate in closely adjacent position relative to said port (34).

4. A sample atomizing device for flameless atomic absorption measurements comprising:
a tube of electrically conducting material which is heatable by passing an electric current therethrough, said tube having at least one port extending through a wall thereof generally at the longitudinal center of the tube, means for causing the tube to be surrounded by an inert protective gas;
said causing means comprising means for generating a flow of said protective gas generally into the ends of said tube (32, 82) so that the gas flows out of said tube through said central port (34, 84);
housing means (10, 66) generally enclosing said tube to define an annular chamber (44, 114) which surrounds the exterior wall of said tube and is therefore in communication with said port (34, 84); and
a protective gas outlet means (48, 116) provided so as to allow said protective gas ultimately to flow from said annular chamber (44, 114) to the exterior of said housing; and
a suction means connected to said protective gas outlet means (48, 116).

5. A sample atomizing device as recited in claim 4, further comprising:
a connection means between said protective gas outlet means and said suction means;
said connection means defining adjustable openings (54, 56) leading to the atmosphere.

6. A sample atomizing device for flameless atomic absorption measurements comprising:
a tube of electrically conducting material which is heatable by passing an electric current therethrough, said tube having at least one port extending through a wall thereof generally at the longitudinal center of the tube, means for causing the tube to be surrounded by an inert protective gas;
said causing means comprising means for generating a flow of said protective gas generally into the ends of said tube (32, 82) so that the gas flows out of said tube through said central port (34, 84);
housing means (10, 66) generally enclosing said tube to define an annular chamber (44, 114) which surrounds the exterior wall of said tube and is therefore in communication with said port (34, 84); and
a protective gas outlet means (48, 116) provided so as to allow said protective gas ultimately to flow from said annular chamber (44, 114) to the exterior of said housing;
said housing means (10, 66) being of basically cylindrical shape and comprises two halves (12, 14; 68, 70);
insulating means (46, 72) positioned between said two halves to electrically insulate them with respect to each other;
each of said halves of said housing means comprising means defining an annular coolant channel (16, 18; 74, 76) therein;
annular electrodes (24, 26; 78, 80) positioned, within and in contact with each of said means defining said annular coolant channels;
each of said annular electrodes contacting an end of said tube (32, 82) so as to hold said tube therebetween.

7. A sample atomizing device as recited in claim 6, in which:
light transmitting windows (40, 42) are positioned on the front surfaces of said housing (10) in coaxial relationship to said tube (32).

8. A sample atomizing device as recited in claim 7, in which:
said protective gas flow generating means comprise a pair or protective gas connection means (62, 64) each of which extends through one of said coolant channels (16, 18) and one of said electrodes (24, 26) and opens in the space surrounded by said electrodes in the vicinity of said windows (40, 42).

9. A sample atomizing device as recited in claim 6, in which:
said housing means (66) comprises end wall defining light transmitting openings (86, 88) coaxially aligned with said tube (82) so that an axial passage channel (90) is obtained;

a pair of annular protective gas channels, (94, 96), each surrounding one of said light transmitting openings (86, 88);

means (98, 100) for supplying protective gas to said annular channels (94, 96);

each of said annular channels being supplied with an annular gap (102, 104) so as to cause protective gas to flow into said passage channel (90) and generally inwardly into said sample tube (82).

10. A sample atomizing device as recited in claim 9, further comprising:

a pair of annular chambers (106, 108) connecting each of said annular gaps (102, 104) to said passage channel (90), said annular chambers gradually enlarging in cross-section as it extends radially from said annular gaps toward said passage channel.

11. A sample atomizing device as recited in claim 9, in which:

said means for supplying protective gas (98, 100) to said annular channels (94, 96) supplies a quantity of protective gas that is substantially greater than the amount of said gas which ultimately flows out of said central port (84) of said tube (82), thereby supplying excess protective gas to said light transmitting openings (86, 88).

* * * * *

UNITED STATES PATENT AND TRADEMARK OFFICE
CERTIFICATE OF CORRECTION

PATENT NO. : 4,098,554
DATED : July 4, 1978
INVENTOR(S) : Bernhard Werner Huber, Rolf Gunther Tamm & Klaus Joachim Braun It is certified that error appears in the above-identified patent and that said Letters Patent are hereby corrected as shown below:

Assignee:
Front page, [73], Change "The Perkin-Elmer Corporation, Norwalk, Conn.
to -- Bodenseewerk Perkin-Elmer & Co., GmbH, Bodenseewerk, Germany --.

Column 1, line 21, change "annular respective" to--respective annular --.

Column 2, line 50 change ". Moreover," to --; moreover,--.

Column 4, line 63, change "desired" to -- described --.

Column 7, line 5-6, change "exceeding" to --extending --.

Column 7, line 15, before "of", insert --wall --.

Column 7, line 38, before "for", insert --means --.

Signed and Sealed this

Thirtieth Day of January 1979

[SEAL]

Attest:

RUTH C. MASON
Attesting Officer

DONALD W. BANNER
Commissioner of Patents and Trademarks